United States Patent
Belyk et al.

(10) Patent No.: US 7,214,768 B2
(45) Date of Patent: May 8, 2007

(54) ECHINOCANDIN PROCESS

(75) Inventors: Kevin M. Belyk, Somerset, NJ (US); William R. Leonard, Basking Ridge, NJ (US)

(73) Assignee: Merck & Co., Inc., Rahway, NJ (US)

( * ) Notice: Subject to any disclaimer, the term of this patent is extended or adjusted under 35 U.S.C. 154(b) by 521 days.

(21) Appl. No.: 10/474,893

(22) PCT Filed: Apr. 8, 2002

(86) PCT No.: PCT/US02/12756

§ 371 (c)(1),
(2), (4) Date: Oct. 10, 2003

(87) PCT Pub. No.: WO02/083713

PCT Pub. Date: Oct. 24, 2002

(65) Prior Publication Data

US 2004/0158034 A1   Aug. 12, 2004

(51) Int. Cl.
*C07K 7/00* (2006.01)
*C07K 7/64* (2006.01)

(52) U.S. Cl. .................. 530/317; 530/318; 530/338; 530/339; 514/2; 514/9; 514/11; 930/270; 930/DIG. 548; 930/DIG. 546

(58) Field of Classification Search .............. 530/317, 530/318, 338, 339; 930/270, DIG. 548, 930/DIG. 546; 514/2, 9, 11
See application file for complete search history.

(56) References Cited

U.S. PATENT DOCUMENTS

| 5,378,804 A | 1/1995 | Balkovec et al. |
| 5,552,521 A | 9/1996 | Belyk et al. |
| 5,936,062 A | 8/1999 | Leonard et al. |
| 5,939,384 A | 8/1999 | Hammond et al. |

OTHER PUBLICATIONS

M. Journet, et al., Semisynthesis of an Antifungal Lipopeptide Echinocandin, 1999, 2411-2417, 64.

*Primary Examiner*—Jon Weber
*Assistant Examiner*—Abdel A. Mohamed
(74) *Attorney, Agent, or Firm*—Richard S. Parr; Valerie J. Camara

(57) ABSTRACT

This invention relates to an improved process for the minimization of acid-catalyzed reactions of certain echinocandins of the kind disclosed in U.S. Pat. No. 5,378,804. The process involves the use of a boronic acid.

18 Claims, No Drawings

ECHINOCANDIN PROCESS

This application is related to PCT application PCT/US02/12756, filed Apr. 8, 2002.

BACKGROUND OF THE INVENTION

This invention relates to an improved process for the minimization of acid-catalyzed reactions of certain echinocandins of the kind disclosed in U.S. Pat. No. 5,378,804. The echinocandin compounds disclosed in the patent have been prepared as described in the patent and in patents claiming improvements of the process. U.S. Pat. No. 5,552,521 discloses a three-step process for preparing the compounds of the invention. U.S. Pat. No. 5,936,062 discloses an improvement of the three-step process using a boronate intermediate. Articles in the *Journal of Organic Chemistry*, 1999, 64, 2411–2417 and *J. Med. Chem.* 1994, 37, 222–225, describe an amide to nitrile dehydration of similar echinocandins using cyanuric chloride. However, the previous processes resulted in the formation of unwanted benzylic substituted derivatives of the desired compound. The instant invention results in increased yield of the desired product while minimizing the acid-catalyzed reaction at the benzylic center as well as acid-catalyzed epimerization at the benzylic center. Additionally, the process allows for the use of moderate to strong acid catalysts previously determined to be ineffective at catalyzing the reaction in a highly chemoselective manner. The improvement permits the use of considerably less acid to complete the formation of the desired compound. Additionally, the α/β stereoselectivity for the phenylsulfide formation reaction is greatly increased.

SUMMARY OF THE INVENTION

This invention is directed to a process for the minimization of certain impurities generated by acid-catalyzed reactions of certain echinocandins. In particular, the invention describes an improvement to the process of preparing certain sulfide-substituted echinocandins formed as intermediates in the preparation of the compound of the structure (I)

This compound has been found useful in treating life-threatening fungal infections.

DETAILED DESCRIPTION OF THE INVENTION

This invention relates to a process for minimizing of certain impurities generated by the acid-catalyzed reactions of certain echinocandins, which results in an improvement to the process for the preparation of certain sulfide-substituted echinocandins required for the preparation of the compound of the structure

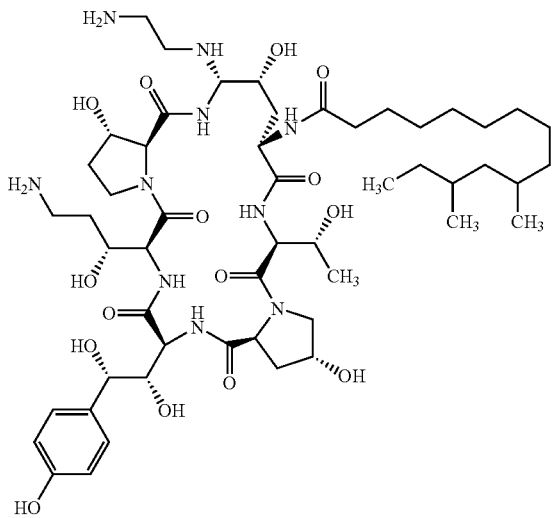

(I)

or its pharmaceutically acceptable salt, hydrate or solvate thereof.

Additionally, the invention relates to an improvement in the preparation of the compound of the structure 1

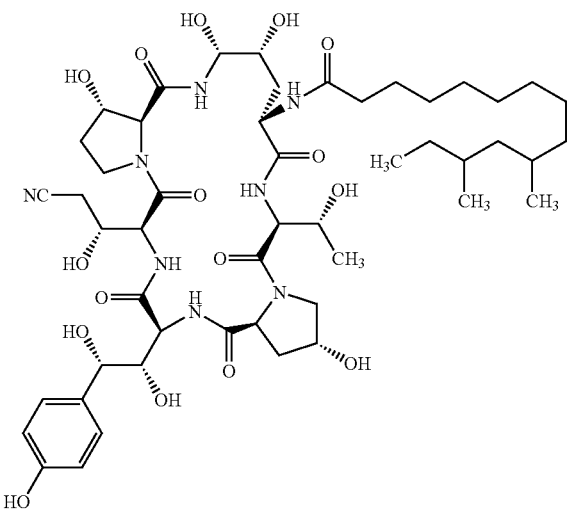

(1)

or its pharmaceutically acceptable salt, hydrate or solvate thereof, from the starting material used to prepare the compound of structure I.

A process for the preparation of a Compound 1 of structure

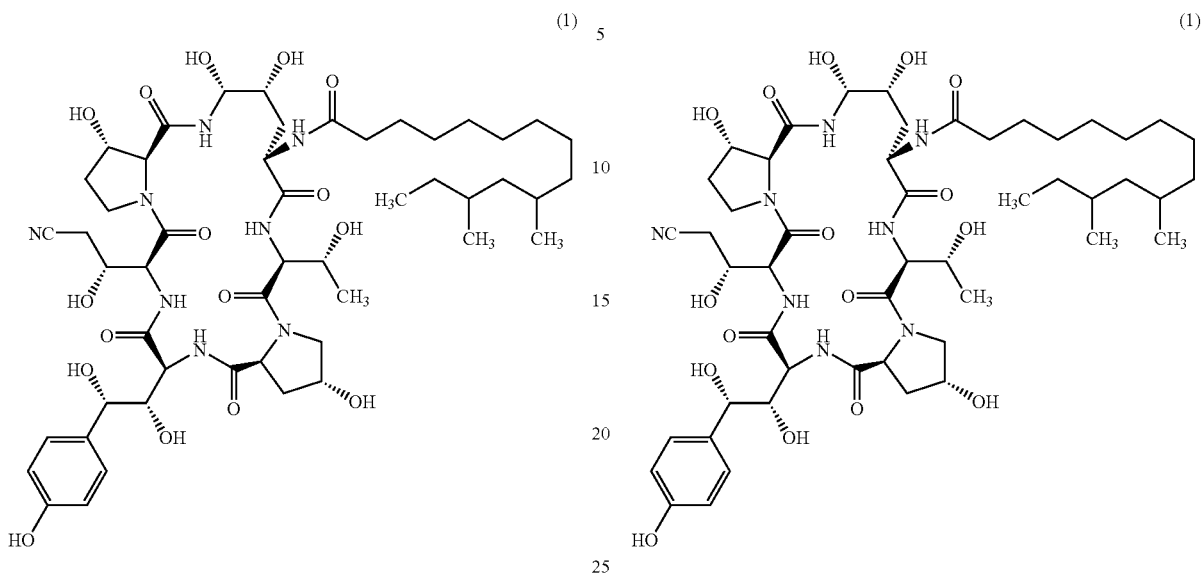

or its pharmaceutically acceptable salt, hydrate or solvate thereof, which comprises the steps of:

a) reacting an amide Compound 2 of the structure

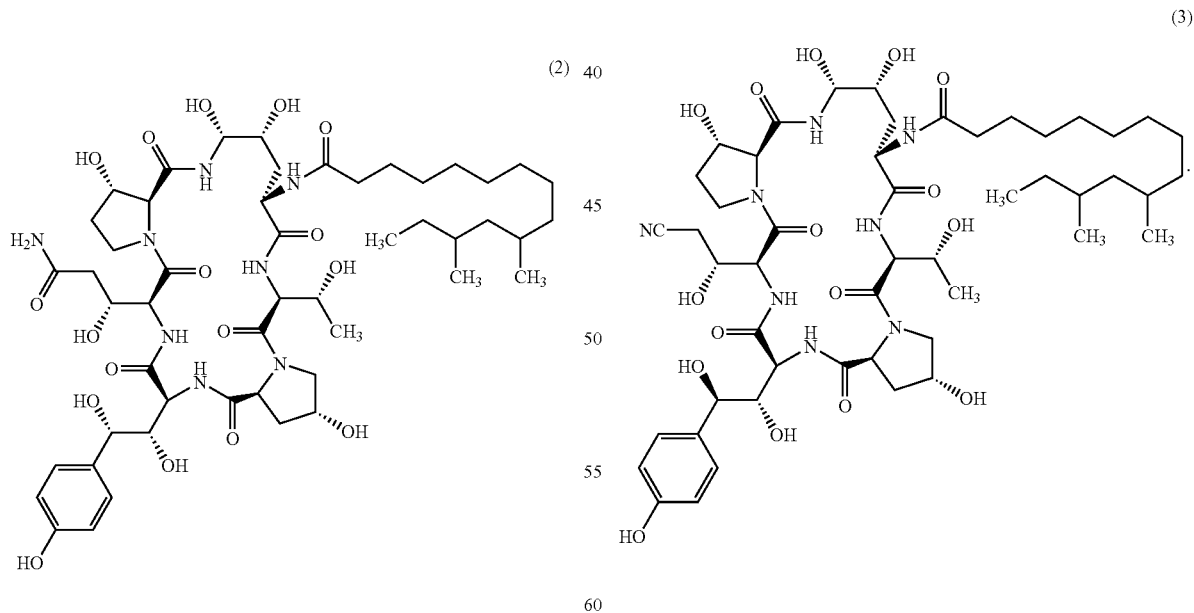

with a boronic acid or borate in a solvent to obtain a boronate or borate, respectively; and b) dehydrating the boronate or borate with cyanuric chloride in a second solvent to produce a nitrile Compound 1 with concomitant formation of a minimal amount of an epimer of the nitrile Compound 1, Compound 3 having the structure Prior processes resulted in the formation of about 3–5% of Compound 3, the benzylic hydroxyl epimer of the nitrile Compound 1. The instant invention reduces the acid-catalyzed epimerization of the benzylic hydroxyl group to <1%.

Compound 2 can be produced by cultivating *Glarea lozoyensis* (formerly identified as *Zalerion arboricola*) ATCC 20868 in a nutrient medium enriched in mannitol as the primary source of carbon, as described in U.S. Pat. No. 5,021,341, issued Jun. 4, 1991. Compound 2 is claimed in U.S. Pat. No. 5,202,309 that issued Apr. 13, 1993. Compound 2 can also be produced by cultivating *Zalerion arboricola* in a nutrient medium enriched the unnatural amino acid selected from the group consisting of: 3,4-dehydroproline, L-azetidine-2-carboxylic acid, L-proline or mixture, as described in U.S. Pat. No. 5,194,377 issued on Mar. 16, 1993.

Step a involves reaction of Compound 2 and a boronic acid in a first solvent. About 100 to about 200 mole % of the boronic acid can be employed, and about 200 mole % of the boronic acid is preferred. Any boronic acid or borate can be used to produce the desired result. Examples of such boronic acids or borates are: phenylboronic acid, 3-nitrophenylboronic acid, 4-methoxyphenylboronic acid, 3,5-bis(trifluoromethyl)phenylboronic acid, n-butylboronic acid, trimethyl borate and triethylborate. A preferred boronic acid is phenyl boronic acid. Examples of such first solvent are tetrahydrofuran, CH3CN or a mixture therefrom.

When formation of the borate/boronic is complete in Step a, the water is removed from the reaction mixture. The water is removed by azeotropic distillation of the reaction solvent with concomitant addition of dry solvent or by passing the refluxate through a bed of molecular sieves until a ratio of less than about 20 mole % water to Compound 2 is obtained.

After removal of the water from the reaction mixture, the solvent is removed in vacuo and subsequent dissolution of the borate/boronate derivative with a second solvent. Suitable second solvent(s) such as dry N,N-dimethylformamide (DMF), tetrahydrofuran, or N-methylpyrrolidinone (NMP) or mixtures thereof can be used. The preferred solvent is a mixture of N-methylpyrrolidinone and N,N-dimethylformamide.

Step b involves dehydration of the borate/boronate derivative in the sutiable second solvent with cyanuric chloride or other appropriate reagent to yield the nitrile. The amount of cyanuric chloride used is crucial to limit the formation of the undesired hydroxyl epimer at the benzylic position of the homo-tyrosine portion of the cyclic peptide. About 100 to about 300 mole % of cyanuric chloride can be employed, and about 180 to about 230 mole % is the preferred range.

A preferred embodiment of this invention is the process wherein about 200 mole % phenylboronic acid in tetrahydrofuran is used in Step a at ambient temperature, followed by removal of water by azeotropic distillation of the refluxate through molecular sieves (3 Å). The reaction mixture is then dried and the solvent removed in vacuo. The resulting solids were dissolved in the second solvent(s) a 9:1 N-methylpyrrolidinone/N,N-dimethylformamide volume to volume mixture and dehydrated with 230 mole % of cyanuric chloride. The cyanuric chloride was added at −13° C. and the reaction mixture was aged at −13° C. to −23° C. for 20 hours. These conditions resulted in a chemical yield of about 84% with no benzylic hydroxyl epimer (Compound 3) detected by HPLC analysis.

In a second embodiment of this invention, there is disclosed an improved process for minimizing the acid-catalyzed reaction of $R^3$—SH at the benzylic center which results in a significantly lower formation of the undesired benzylic-substituted bissulfide derivative, 5B. Prior processes resulted in >9% of the undesired benzylic-substituted bis(phenylsulfide) derivatives, 5B (wherein $R^3$—SH is thiophenol). This process, wherein $R^3$—SH is thiophenol, also results in an increase in chemical yield to about 92% to about 95% with the formation of only about 2–3% of the undesired benzylic-substituted bis(phenylsulfide) derivatives. The improved process allows for the use of strong acid catalysts previously determined to be ineffective due to excessive substitution or epimerization of the benzylic hydroxyl group. In addition, the improved process allows for the use of significantly less acid to complete the sulfide formation. The sulfide compound, 5A is a key intermediate in the preparation of the compound of Structure I.

This embodiment of the invention discloses, a process for preparing Compound 5A of the structure

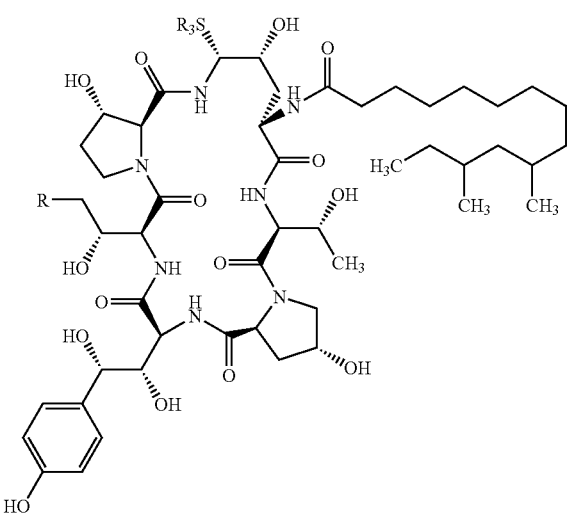

(5A)

or pharmaceutically acceptable salt, hydrate or solvate thereof, while minimizing the formation of Compounds 5B and Compound 5C of the structure

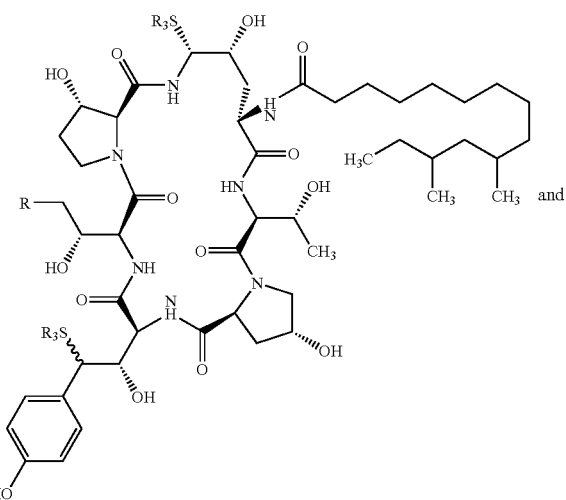

(5B)

and

-continued

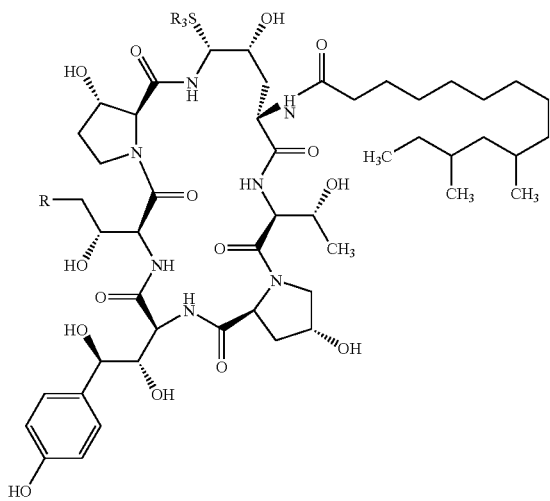

(5C)

wherein

R is C(=O)NH$_2$, CH$_2$NH$_3$+X— or CN;

X— is Cl$^-$, CF$_3$COO$^-$, CH$_3$COO$^-$, CF$_3$SO$_3^-$, HSO$_4^-$; and

R$_3$ is aryl, wherein aryl is defined as phenyl or naphthyl, substituted or unsubstituted with C$_1$–C$_6$-alkyl, C$_1$–C$_6$-alkoxy, halo (Br, Cl, F, I), (CH$_2$)aryl, heteroaryl, wherein heteroaryl is defined as 5-membered ring, 6-membered ring, 5,6-fused ring, or 6,6-fused ring bearing 1 to 3 heteroatoms selected from N, O, or S optionally substituted with C$_1$–C$_6$-alkyl, or C$_1$–C$_6$-alkoxy;

which comprises the steps of:

A) reacting Compound 4 of the structure (4)

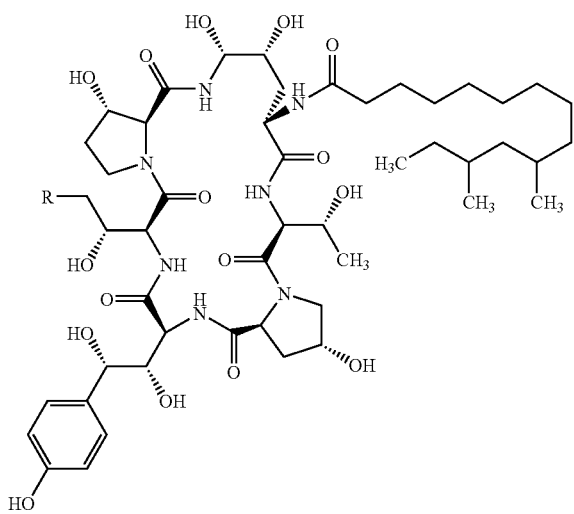

with a boronic acid or borate in a solvent to afford boronate(s) or borate(s), respectively, of compound 4; and B) reacting the boronate or borate with a thiol, R$_3$SH, wherein R$_3$ is as defined above, and an acid to afford Compound 5A with minimal amounts of Compounds 5B and 5C.

The sulfide, Compound 5A is prepared by formation of the boronate/borate in Step A which comprises reaction of Compound 4 (Compound 2, R=C(=O)NH$_2$; Compound 1, R=CN or Compound 6, R=CH$_2$NH$_3$+X—) with a boronic acid, R$_1$B(OH)$_2$, or borate, (R$_2$O)$_3$B, in a solvent; followed by reaction of the boronate/borate produced in Step A with a thiol, R$_3$SH, and an acid, R$_4$—H+, in Step B to produce the sulfide, Compound 5A.

Solvent(s) such as tetrahydrofuran, acetonitrile, or mixtures thereof can be used in reaction Step A. Any boronic acid or borate is expected to produce the desired results. Examples of such boronic acid or borate include, but are not limited to, phenylboronic acid, 3-nitrophenylboronic acid, 3,5-bis(trifluoromethyl)phenyl-boronic acid, 4-methoxyphenylboronic acid, n-butylboronic acid, trimethyl borate and triethyl borate. The reaction is carried out at a temperature range of about 20° C. to about 66° C. and for a reaction time of about 15 minutes to about 12 hours.

The Compound 4, wherein R represents CH$_2$NH$_3$+X— (also referred to as Compound 6) is prepared by chemical or catalytic reduction of the nitrile compound, Compound 1. Chemical reduction can be carried out using sodium borohydride, aluminum hydride, diborane, diisobutyl aluminum hydride and the like. Catalytic reduction may also be employed using hydrogenation with a variety of catalysts including palladium on carbon, platinum oxide, or rodium on alumina. See U.S. Pat. No. 5,939,384 and the *Journal of Organic Chemistry*, 1999, 64, 2411–2417.

A preferred embodiment of this invention is the process Step A as recited above, wherein the boronic acid is phenylboronic acid and the solvent is CH$_3$CN.

Following the formation of the boronate/borate in Step A, the boronate/borate product is combined with a thiol and suitable acid in Step B to yield the desired sulfide, Compound 5A in a highly stereoselective and chemoselective manner. Any thiol is expected to produce the sulfide intermediate. R$_4$—H+ represents a suitable acid, a moderate to strong acid that would be expected to produce the sulfide intermediate in good yield. Examples of such moderate to strong acids include, but are not limited to, trifluoroacetic acid, methanesulfonic acid, p-toluenesulfonic acid, and trifluoromethanesulfonic acid.

A preferred embodiment of this invention is the process Step A as recited above, wherein the thiol is thiophenol and the R$_4$—H+ is trifluoromethanesulfonic acid.

When reaction Step B is complete, the mixture is quenched with water or dilute base and, following an annealing step, the sulfide intermediates are isolated by filtration.

The amount of boronic acid or borate used is crucial to the rate of displacement, as well as to the formation of the undesirable bis(sulfide) derivative (Compound 5B) and benzylic hydroxyl epimer (Compound 5C). It was found that from about 100 to about 900 mole % of a boronic acid or a borate gave the best yield of Compound 5A with about 100 to about 300 mole % of the boronic acid being the preferred range.

The amount of thiol used in the sulfide formation step is also critical to the yield of Compound 5A. About 200 to about 500 mole % of thiophenol provided the best yield of the phenylsulfide intermediate (Compound 5A).

The amount of R$_4$—H+ used is also critical to the yield of Compound 5A and formation of the undesired Compounds 5B and 5C. It was found that about 200 to about 4600 mole % of a moderate to strong acid catalyst gave the best yield. Additionally, the conditions provide optimal process aging time, chemoselectivity, stereoselectivity, and the best means of producing an easily filtered product.

A preferred embodiment of the invention is the process as recited above wherein Compound 4 is reacted with about 200 mole % of phenylboronic acid in acetonitrile at ambient temperature for about 0.5 hours followed by reaction of the boronate with 300 mole % thiophenol and about 300 mole % trifluoromethanesulfonic acid at about −13° C. HPLC analysis showed a chemical yield of about 95% with concomitant formation of about 3 area % of the bis(phenylsulfide) and 0.1 area % of the benzylic hydroxyl epimer, Compounds 5B and 5C respectively. The reaction mixture is diluted to 90% acetonitrile/10% water (v/v) with water containing 300 mole % sodium acetate. The product was isolated by filtration after an annealing step. The phenylsulfide intermediate was isolated in about 91%. yield and contained 1.1 area % of the undesired benzylic-substituted bis(phenylsulfide) derivative (Compound 5B) and <0.1 area % of the undesired benzylic hydroxyl epimer (Compound 5C) as analyzed by HPLC.

An additional embodiment of the process for preparing the sulfide Compound 5A, is the process which includes the additional steps of:
(i) quenching the reaction mixture containing Compound 5A with aqueous base and cooling the reaction mixture to precipitate Compound 5A as a suspension of fine amorphous particles of Compound 5A;
(ii) warming the suspension of Compound 5A to about 15 to about 25° C. over about 1.5 to 2.0 hours to produce larger amorphous particles of Compound 5A and aging the suspension of Compound 5A for about 20 to about 30 minutes at about 15 to about 25° C.;
(iii) cooling the suspension with larger amorphous particles of Compound 5A to 0° C. and aging the suspension of Compound 5A for about 1 hour; and
(iv) filtering the suspension of larger amorphous particles of Compound 5A to isolate larger amorphous particles of Compound 5A.

The invention is described in greater detail in the following examples in which all parts, preparations, ratios and percentages are by weight unless otherwise indicated.

EXAMPLE 1

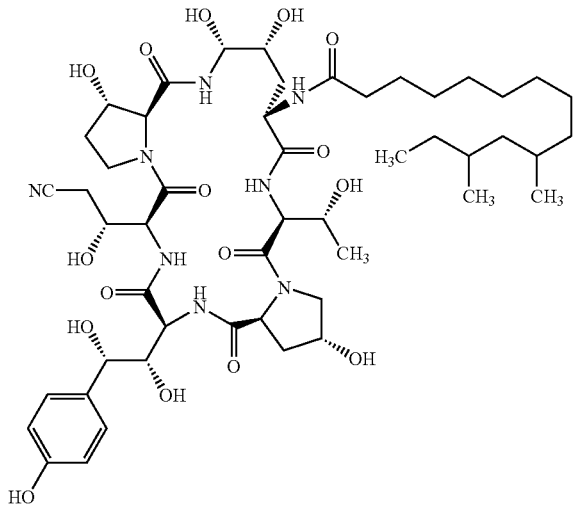

1

Synthesis of Compound 1

The amide, Compound 2, (1.0 g, 0.94 mmole) and phenylboronic acid (235 mg, 1.90 mmole) were added to dry tetrahydrofuran (10 mL) and the suspension was agitated until all solids dissolved (40 min). The resulting solution was dried to <20 mol % water: Compound 2 by passing the refluxate through a bed of molecular sieves (3A). A portion of the dried solution (1.0 mL) containing Compound 2 boronate (120 mg, 0.12 mmole) was transferred to a 25 mL flask where the tetrahydrofuran was removed under vacuum. The resulting solid was dissolved in 4.0 mL dry 1-methyl-2-pyrrolidinone and 0.45 mL dry N,N-dimethylformamide at ambient temperature. Cyanuric chloride (50 mg, 0.27 mmole) was then added at −13° C. with stirring. The reaction was aged for 2.5 hours at −13° C. followed by 18 hours at −23° C. HPLC analysis (210 nm) showed 3 area % Compound 2 and an 84% yield of Compound 1. Compound 3 was not detected by HPLC at this time nor was it observed after an additional 26 hours of the reaction at −20° C.

EXAMPLE 2

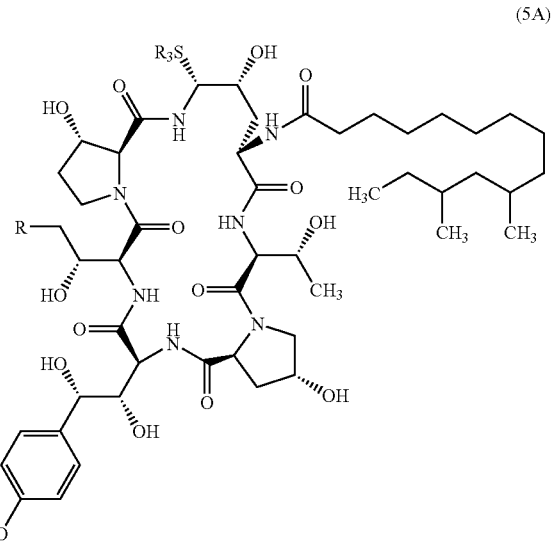

(5A)

Synthesis and Isolation of Compound 5A (R=C(=O)NH$_2$, R$_3$=phenol)

Compound 4 (R=C(=O)NH$_2$, 23.1 g, 21.7 mmole) and phenylboronic acid (5.72 g, 46.9 mmole) were added to dry acetonitrile (750 mL). The suspension was stirred at ambient temperature for 0.5 hours and then cooled to −6° C. where thiophenol (7.24 mL, 70.4 mmole) was added. Trifluoromethanesulfonic acid (6.23 mL, 70.4 mmole) was then added over 10 minutes while maintaining a temperature of −13° C. The reaction progress was monitored by HPLC until the ratio of starting material/product was 1:99 (2 hours). The chemical yield of phenylsulfide intermediate for the reaction was 95% as a 60:1 mixture of α- and β-diastereomers by HPLC assay. The undesired benzylic-substituted bis(phenylsulfide) derivative (Compound 5B, R=C(=O)NH$_2$, R$_3$=phenyl) and the undesired benzylic hydroxyl epimer (Compound 5C, R=C(=O)NH$_2$, R$_3$=phenyl) were present at 3.2 HPLC area % (210 nm) and 0.1 HPLC area % (210 nm), respectively. At 2.5 hours, a solution of NaOAc$_3$H$_2$O (9.58 g, 70.4 mmole) in 80 mL water was added at a rate so as to maintain the temperature below −9° C. The product precipitated as 1–2 μm amorphous particles. The suspension was warmed to 19° C. over 1.25 hours during which the amorphous precipitate turned over to 5–25 μm amorphous particles. The suspension was then aged 20 minutes at 19° C. and then cooled to 0° C. and aged 1 hour. The solids were removed by filtration and washed with 3×100 mL of 9:1 acetonitrile:water (v/v). The material was then dried under a nitrogen flow. The assay yield of the phenylsulfide was 22.7 g (91%) as a 180:1 mixture of α- and β-diastereomers. The solid contained 1.1 HPLC area % (210 nm) of the undesired benzylic-substituted bis(phenylsulfide) derivative (Compound 5B, R=C(=O)NH$_2$, R$_3$=phenyl) and <0.1 HPLC area % (210 nm) of the undesired benzylic hydroxyl epimer (Compound 5C, R=C(=O)NH$_2$, R$_3$=phenyl) by BPLC analysis.

What is claimed is:

1. A process for preparing Compound 5A of the structure

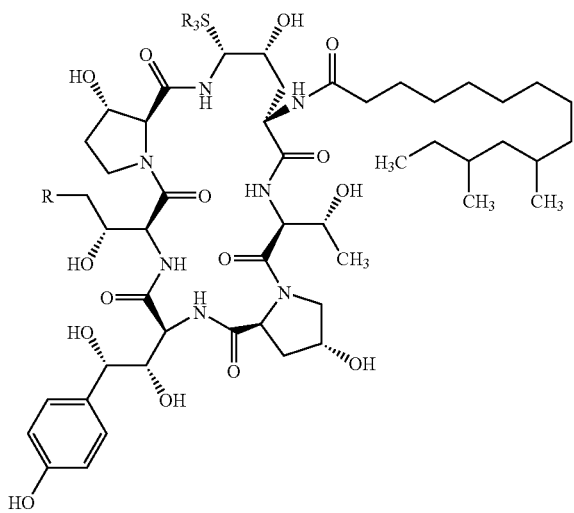

(5A)

while minimizing the formation of Compounds 5B and Compound 5C of the structure

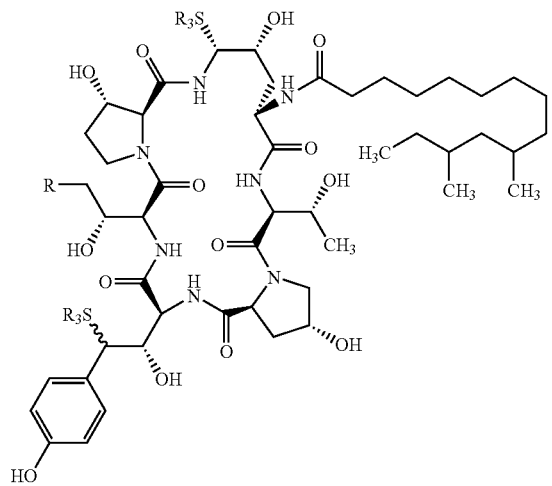

(5B)

and

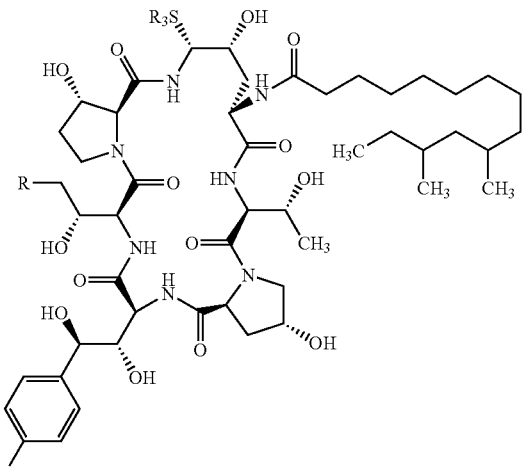

(5C)

or their pharmaceutically acceptable salts, hydrates or solvates thereof, which comprises the steps of:

A) reacting Compound 4 of the structure

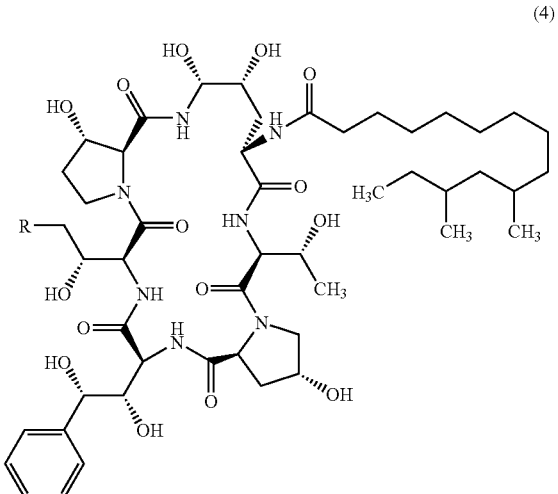

(4)

wherein

R is C(=O)NH$_2$, CH$_2$NH$_3$+X— or CN;

X— is Cl$^-$, CF$_3$COO$^-$, CH$_3$COO$^-$, CF$_3$SO$_3^-$, HSO$_4^-$; and

R$_3$ is aryl, wherein aryl is defined as phenyl or naphthyl, substituted or unsubstituted with C$_1$–C$_6$-alkyl, C$_1$–C$_6$-alkoxy, halo (Br, Cl, F, I), (CH$_2$)aryl, heteroaryl, wherein heteroaryl is defined as 5-membered ring, 6-membered ring, 5,6-fused ring, or 6,6-fused ring bearing 1 to 3 heteroatoms selected from N, O, or S optionally substituted with C$_1$–C$_6$-alkyl, or C$_1$–C$_6$-alkoxy;

with a boronic acid or borate in a solvent to afford boronate(s) or borate(s), respectively, of compound 4; and B) reacting the boronate or borate with a thiol, R$_3$SH, wherein R$_3$ is as defined above, and an acid in the amount of 1 eq. of the thiol $R_3SH$ to afford Compound 5A with minimal amounts of Compounds 5B and 5C.

2. The process of claim 1, further comprising the additional steps of:
(i) quenching the reaction mixture containing Compound 5A with aqueous base and cooling the reaction mixture to precipitate Compound 5A as a suspension of fine amorphous particles of Compound 5A;
(ii) warming the suspension of compound 5A to about 15 to about 25° C. over about 1.5 to 2.0 hours to produce larger amorphous particles of Compound 5A and aging the suspension of Compound 5A for about 20 to about 30 minutes at about 15 about 25° C.;
(iii) cooling the suspension with larger amoiphous particles of Compound 5A to 0° C. and aging the suspension of Compound 5A for about 1 hour; and
(iv) filtering the suspension of larger amorphous particles of Compound 5A to isolate larger amorphous particles of Compound 5A.

3. The process of claim 1, wherein the boronic acid or borate in Step A is selected from the group consisting of: myl boronic acid, wherein aryl is defined as phenyl, 1- or 2-naphthyl, 9-anthryl or phenmntbryl, unsubstituted or substituted with 1, 2 or 3 substitutents selected from the group consisting of: nitro, $C_1$–$C_6$-alkyl, $C_1$–$C_6$-alkoxy, halo (Br, Cl, F, I), and trifluoromithyl, $C_1$–$C_6$-alkyl boronic acid, or tri($C_1$–$C_6$-alkyl) borate.

4. The process of claim 3, wherein the solvent used in Step A is tetrahydrofuran, $CH_3CN$ or a mixture therefrom.

5. The process of claim 4 wherein the thiol, $R_3SH$ used in Step B is selected from the group consisting of: thiophenol, 4-methoxythiophenol, benzylthiol, 1-methylixnidazol-2-ylthiol, and benziniidazol-2-ylthiol.

6. The process of claim 5, wherein the acid used in Step B is selected from the group consisting of: trifluoroacetic acid, methanesulfonic acid, p-tohzenesnlfonic acid, and trifluoromethaneaulfonic acid.

7. The process of claim 6, wherein the boronic acid used in Step A is phenylboronic acid.

8. The process of claim 7, wherein the solvent used in Step A is $CH_3CN$.

9. The process of claim 8, wherein the acid used in Step B is trifluoromethanosulfonic acid.

10. The process of claim 9, wherein the thiol, $R_3SH$ used in Step B is thiophenol.

11. The process of claim 10, wherein about 100 to about 300 mole % of phenylboronic acid is used in Step B.

12. The process of claim 11, wherein about 200 to about 500 mole % of the thiophenol is used in Step B.

13. The process of claim 12, wherein the reaction in Step B takes place at a temperature of about −5° C. to about −20° C.

14. The process of claim 8, wherein the acid used in Step B is trifluoroacetic acid.

15. The process of claim 14, wherein the thiol, $R_3SH$ used in Step B is thiophenol.

16. The process of claim 15, wherein about 300 mole % of phenylboronic acid is used in Step B.

17. The process of claim 16, wherein about 200 to 500 mole % of the thiophenol is used in Step B.

18. The process of claim 17, wherein the reaction in Step B takes place at a temperature of about −10° C. to +5° C.

* * * * *